Figure 4:
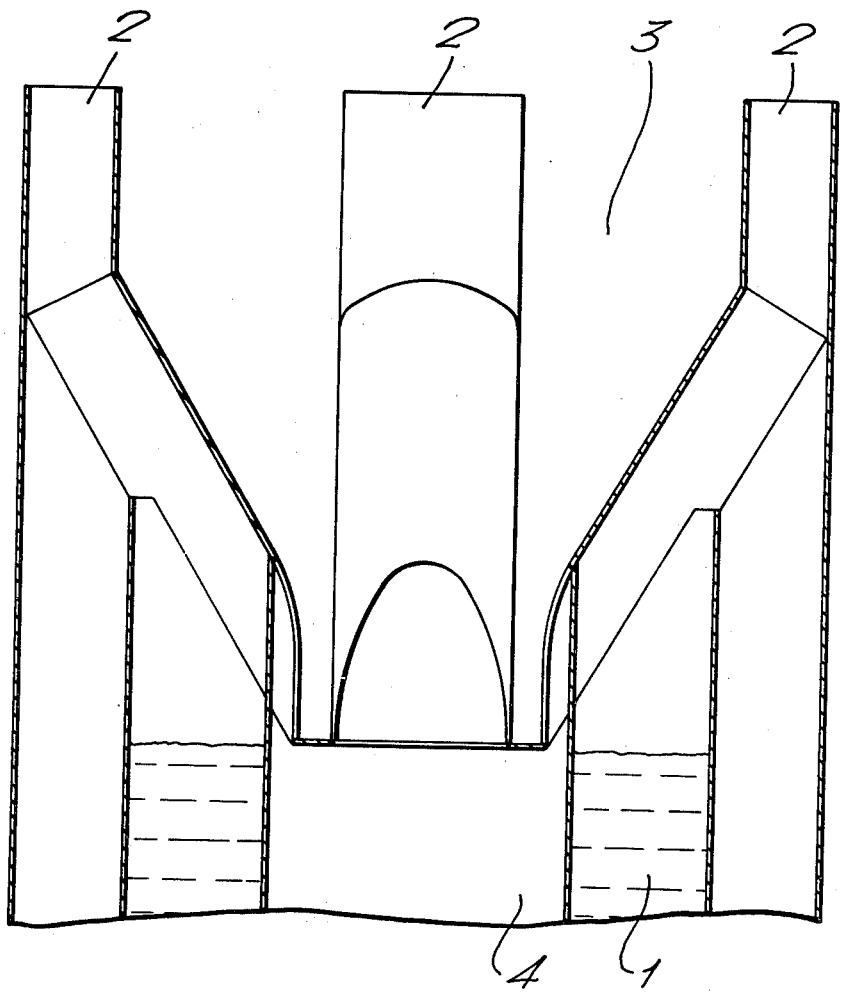

United States Patent [19]
Roesler et al.

[11] 4,183,787
[45] Jan. 15, 1980

[54] CIRCULATION OF GAS/LIQUID MIXTURES

[75] Inventors: Frank C. Roesler; David A. Hines; Frank P. Maslen; Richard Fawcett, all of Stockton-on-Tees, England

[73] Assignee: Imperial Chemical Industries Limited, London, England

[21] Appl. No.: 845,410

[22] Filed: Oct. 25, 1977

Related U.S. Application Data

[63] Continuation of Ser. No. 636,612, Dec. 1, 1975, abandoned.

[30] Foreign Application Priority Data

Dec. 4, 1974 [GB] United Kingdom ............... 52430/74

[51] Int. Cl.² .......................... C12B 1/14; C12B 1/16
[52] U.S. Cl. .................................. 435/43; 261/36 R; 435/314; 435/144; 435/234; 435/106

[58] Field of Search ...................... 195/109, 142, 143; 261/36 R

[56] References Cited

U.S. PATENT DOCUMENTS

3,847,748  11/1974  Gibson et al. ...................... 195/109

*Primary Examiner*—Alvin E. Tanenholtz
*Attorney, Agent, or Firm*—Cushman, Darby & Cushman

[57] ABSTRACT

A method and apparatus for continuously circulating a mixture comprising a liquid and a gas around a system comprising a riser and a downcomer and a gas disengagement section in which liquid flows downwardly at a velocity which does not exceed 0.2 meters per second and is being injected into a lower section of the riser. The method and apparatus are particularly useful for conducting aerobic fermentations.

4 Claims, 5 Drawing Figures

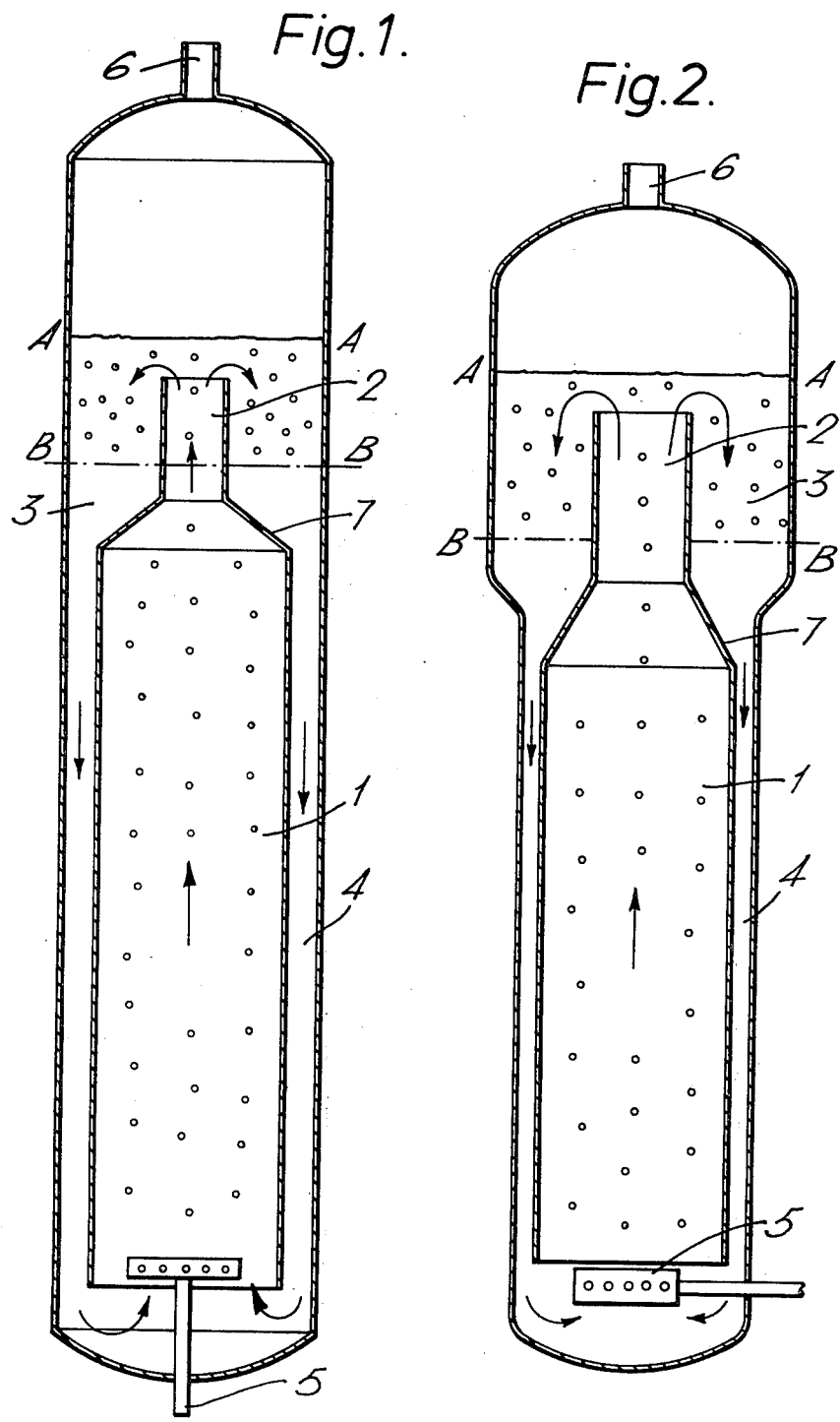

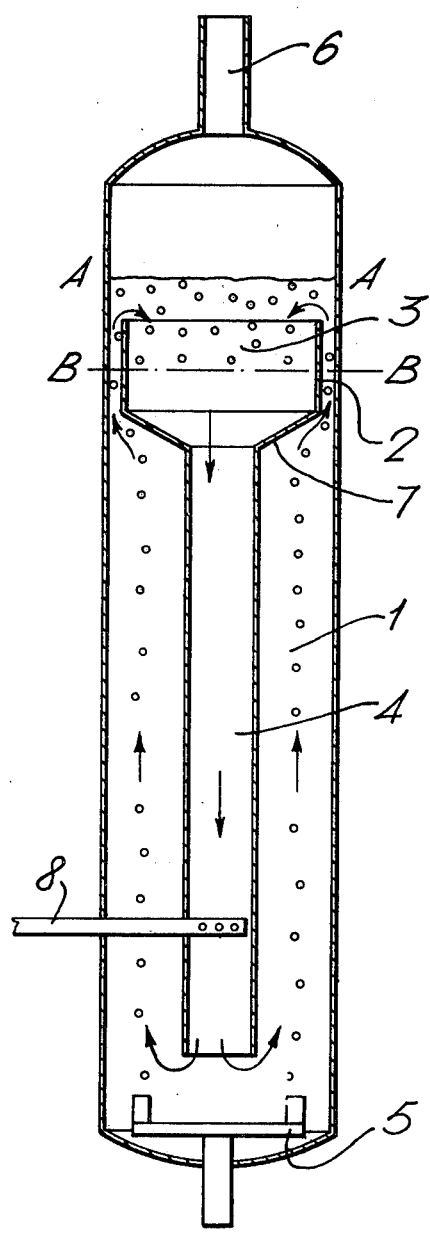
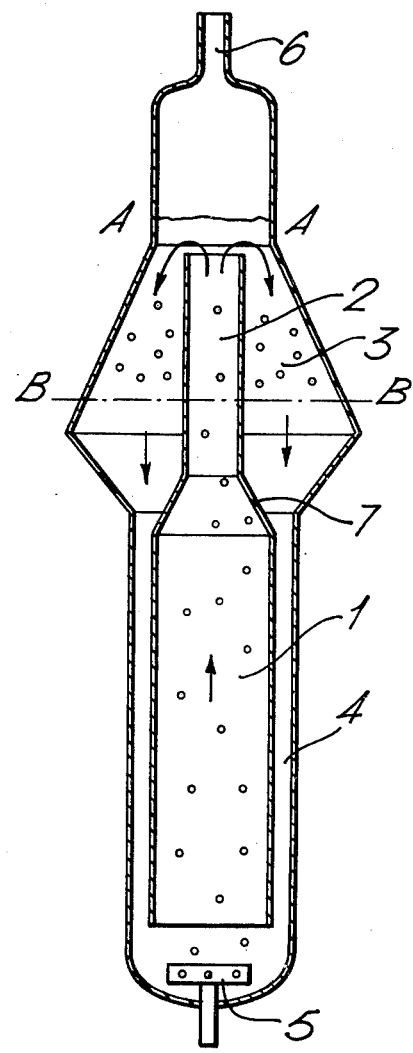

CIRCULATION OF GAS/LIQUID MIXTURES

This is a continuation of application Ser. No. 636,612 filed Dec. 1, 1975, now abandoned.

This invention relates to a method and apparatus for circulating mixtures comprising a gas and a liquid particularly in circumstances wherein it is desirable that efficient disengagement of the gas from the liquid should occur. The invention is especially suitable for use in aerobic fermentations.

Large-scale industrial fermentations, for example, processes for the production of single-cell-protein, are conveniently conducted in 'pressure-cycle' fermenters, for example, fermenters such as those described in our UK Specifications Nos. 1 353 008, 1 417 486 and 1 417 487. In such fermenters a culture is continuously circulated around a system comprising a compartment of ascending flow or riser and a compartment of descending flow or downcomer connected at their upper and lower ends, aeration and circulation of the culture being achieved by sparging air into the lower part of the riser.

It is necessary for such 'pressure-cycle' fermenters to have means for disengaging air which has been bubbled through the circulating culture. Thus there must be a section at the upper end of the fermenter in which the liquid culture has a free surface. Air bubbles rise to this free surface and air is then disengaged from the liquid culture.

The air-disengagement section can be a horizontal tube connecting the upper ends of the riser and the downcomer and which, during operation of the fermenter, is filled with liquid culture to about half-level. The essential functional parameter of the air-disengagement section is the area of the free liquid surface. The area required for air disengagement under ideal conditions can be calculated from equation (1):

$$\text{Area} = \frac{\text{Liquid circulation rate}}{\text{Bubble rising velocity}} \quad (1)$$

The assumption of ideal conditions presupposes inter alia that (a) the motion of the liquid itself is uniform and (b) there is little variation in the bubble rising velocity. In practice (b) is effectively true but (a) is not since the liquid motion is highly turbulent. As a result the area calculated from equation (1) is too small and we have found that in practice it is necessary to double the area calculated from equation (1) in order to effect efficient disengagement.

According to the present invention we provide a method for circulating a mixture comprising a liquid and a gas wherein the mixture is continuously circulated around a system comprising a riser communicating at its lower end with the lower end of a downcomer and at its upper end communicating through a gas disengagement section with the upper end of the downcomer, the riser having an upper section and a lower section, the lower section being of greater cross-sectional area than the upper section, gas being injected into the liquid in the lower section of the riser and being disengaged from the liquid in the gas disengagement section in which liquid flows downwardly at a velocity which does not exceed 0.2 meters per second.

Also according to the invention we provide apparatus for circulating a mixture comprising a liquid and a gas which comprises a riser communicating at its lower end with the lower end of a downcomer and communicating at its upper end through a gas disengagement section with the upper end of the downcomer, the riser having an upper section and a lower section, the lower section being of greater cross-sectional area than the upper section, means being provided in the lower section of the riser for gas to be injected thereinto, the gas disengagement section being designed to allow gas bubbles to disengage from the liquid as it flows downwardly through the gas disengagement section at a velocity not exceeding 0.2 meters per second.

The method and apparatus of the invention is suitably used in an aerobic fermentation process and throughout this specification the invention will be described in terms of such a process. It should be understood however that the method and apparatus of the invention may be used in any process wherein a gas is injected into a liquid and the resulting mixture is circulated and in which disengagement of the gas from the liquid takes place.

The shape of the fermenter of the invention is such that gas disengagement is more efficient and thus it is necessary to increase the area calculated from equation (1) by about 20% only rather than doubling it for practical design. It is a feature of the design that the rate of circulation is automatically limited by the maximum velocity of 0.2 m/s in the gas disengagement section.

The riser of the fermenter suitably has two principal sections, the lower section having the larger cross-sectional area and providing most of the useful fermentation volume. Preferably the cross-sectional area of the lower section is within the range three to six times that of the upper section. The function of the upper section is to increase the pressure in the lower section and also to contribute to the hydraulic driving forces, by virtue, of the difference between the voidage in the upper section and in the downcomer.

For convenience throughout this specification the upper and lower sections of the riser will be referred to as the 'spout' and the 'pot' respectively.

Preferably the disengagement section is constructed as a vessel surrounding the 'spout' and occupying that part of the fermenter volume above the 'pot' which is not occupied by the 'spout'. This gives a vessel which is structurally strong and which can be constructed without external supports. Depending upon the required velocity of flow in the riser the cross-sectional area of the disengagement section may exceed that of the 'pot' in which case the fermenter vessel has a 'club' shape.

In the fermenter described in the preceding paragraph the riser occupies the central region of the fermenter and the disengagement section and the downcomer surround it. It is equally possible and is preferred in some cases that the disengagement section and the downcomer should be in the centre and the 'pot' and the 'spout' should form annuli around them. In this case the 'spout' may be one complete annulus or it may be divided into a plurality of, for example half-circular branches.

In the disengagement section the direction of liquid flow is opposite to that in the 'spout' and therefore is downwards. Any gas bubbles in this section will rise upwards ie countercurrent to the liquid flow.

For convenience throughout this specification the disengagement section will be referred to as the 'choke' and the downcomer will be referred to as the 'sink'.

In the 'pressure-cycle' fermenter the flow is caused by the difference in voidage between the riser and the downcomer. This in the apparatus of the invention the downward velocity of liquid in the 'choke' cannot exceed the natural rising velocity of the bubbles, since otherwise the bubbles will be dragged downwards and the voidage differences between the riser and the downcomer will disappear.

In practice for small gas rates when the circulation velocity is limited by hydraulic losses all the bubbles from the 'spout' rise to the free surface and are disengaged. As the air rate is raised and the circulation velocity increases part of the gas is carried down into the 'choke'. The driving force is diminished and the system settles down to a state wherein the bubble cloud which has formed in the 'choke' extends downwardly to a certain level but no further. The net effect is that the liquid velocity in the 'choke' is controlled to a value of about 0.2 meters/second. As a result, as far as the size of the disengagement area is concerned equation (1) applies if the velocity is taken as 0.2 m/s which represents only an allowance of about 20% compared to the typical bubble rising velocity of 0.25 m/s.

The apparatus of the invention may include a heat exchanger which when the apparatus is a fermenter can serve as a cooler to prevent the temperature of the circulating culture from rising above the optimum temperature for growth of the microorganisms in the culture. In large fermenters the cooler may be situated in either the 'sink' or the 'pot' or it may form their junction. Preferably the fermenter has an overall diameter of at least 4 meters. The 'pot', 'spout', 'choke' and 'sink' may all be contained within the same outer shell.

Preferably the apparatus is a fermenter having a height of at least 20 meters, especially 30 to 50 meters. With smaller fermenters, up to eg. 30 meters in height, the velocity of liquid flow in the 'pot' is suitably approximately the same as in the 'choke' and then the cross-sectional areas of these parts may suitably be the same. In taller fermenters when the liquid velocities in the 'pot' and 'choke' are the same, the liquid circulation time is greater than is necessary for optimum mass transfer of an oxygen-containing gas into the circulating culture. In such fermenters (eg a fermenter of overall height 50 meters with a 'pot' 35 meters high) it is preferred that the cross-sectional area of the 'choke' is increased for example to about twice the cross-sectional area of the 'pot'. In a fermenter where both the riser and downcomer are located inside a single vessel this will involve an overhang of the 'choke' over the combination of 'pot' and 'sink'. Although this is structurally undesirable the required overhang is not great and is less than would be necessary for a disengagement section with horizontal flow in an otherwise similar fermenter. The overhang may be reduced by constructing the 'choke' in a roughly conical shape instead of a cylindrical shape.

The main point of gas entry is into the lower part of the riser. However smaller amounts of gas may be sparged into the system at other places particularly into the downcomer. Gas sparged into the 'sink' where the liquid velocity is sufficiently large to carry bubbles downwards can be used to improve mass transfer of gas into the circulating liquid and to reduce compression costs. Gas may also be sparged into the 'choke' and, during start-up of the apparatus, into either the 'pot' or 'spout' in the area where they join one another.

The apparatus of the invention may be used for fermenters of any type, particularly for very large fermenters. It is also suitable for relatively small auxiliary fermenters eg. for inoculation and effluent treatment in a single-cell-protein production process. As examples of processes in which the invention is useful there may be mentioned, single-cell-protein production such as by growing bacteria upon a hydrocarbon or oxygenated hydrocarbon (eg methanol)—containing substrate, processes for producing amino—and other organic acids (eg citric acid) and processes for producing enzymes (eg glucose isomerase) and antibiotics (eg penicillin).

Typical preferred liquid velocities in the various sections of the apparatus are as follows:
'choke'—0.01 to 0.20 meters/sec.
'sink'—2.0 to 2.5 meters/sec.
'pot'—0.3 to 0.6 meters/sec.
'spout'—2.0 to 2.5 meters/sec.

Suitably the length of the 'choke' is approximately the same as that of the 'spout' and the length of the 'pot' is approximately the same as that of the 'sink'. The effective cross-sectional areas of the 'sink' and the 'spout' are preferably approximately the same.

The outer shell of the apparatus preferably encloses spaces above and below the riser/downcomer system. The upper space suitably contains foam separators or cyclones whilst the lower space can contain a heat exchanger. The spargers for sparging gas into the lower part of the riser may be located in the lower space below the lower end of the riser.

The geometrical arrangements of preferred forms of the apparatus of the invention enable useful savings in fermenter size and complexity to be achieved and can produce improvements in flow control.

Many geometrical arrangements are possible, whilst for most cases, particularly larger fermenters, coaxial and symmetrical arrangements are preferred, non-coaxial and non-symmetrical arrangements are not excluded. For instance in the construction of smaller fermenters various constraints particularly regarding maintainance access may require construction of a fermenter having a non-coaxial and/or non-symmetrical geometry.

The invention is illustrated by the accompanying drawings wherein FIGS. 1 to 5 are diagramatic representations of five variants of fermenters according to the invention.

Each variant has a riser comprising a 'pot' 1 and 'spout' 2 connected through a reducing section 7. Each variant also has a 'choke' 3 and a 'sink' 4. 'Spouts' 2 open into 'chokes' 3 which are connected to 'sinks' 4 whose lower ends communicate with 'pots' 1. Air is sparged into the lower parts of 'pots' 1 through spargers 5 causing culture contained in the fermenters to rise upwardly in the risers and to flow over into 'chokes' 3 and thence pass into 'sinks' 4. Culture fills the fermenters up to the levels A—A, the region above levels B—B in the 'chokes' being occupied by bubbly culture. It is from the region above levels B—B in 'chokes' 3 that gas disengages from the culture to escape through ports 6 at the upper ends of the fermenters. The 'spouts' 2 and 'chokes' 3 and also the 'sinks' 4 and 'pots' 1 are coaxially located, the 'chokes' and the 'sinks' surrounding the risers in FIGS. 1, 2 and 5 and the risers surrounding the 'chokes' and 'sinks' in FIGS. 3 and 4. In FIGS. 2 and 4 'chokes' 3 overhang 'sinks' 4, the 'choke' 3 of FIG. 2 being cylindrical whilst that of FIG. 5 is of conical shape. In the fermenter of FIG. 3 additional air may be sparged into 'sink' 4 by sparger 8. FIG. 4 shows the upper part of a fermenter in which 'spout' 2 is divided into a plurality of branches each branch being of half circular cross-section.

We claim:

1. A method for circulating a mixture comprising a liquid and a gas which comprises the steps of continuously circulating the mixture around a system comprising a riser communicating at its lower end with the lower end of a downcomer and at its upper end communicating through a gas disengagement section with the upper end of the downcomer, the riser having an upper section and a lower section, the lower section being of greater cross-sectional area than the upper section, injecting a gas into the liquid in the lower section of the riser and disengaging a substantial portion of the gas injected into the liquid from downwardly flowing liquid in the gas disengagement section, in which section the liquid flows downwardly at a velocity which does not exceed 0.2 meters per second.

2. A method according to claim 1 wherein the liquid is a culture comprising aerobic microorganisms and the gas is an oxygen-containing gas.

3. A method according to claim 1 wherein the liquid velocity in the gas disengagement section is between 0.01 and 0.20 meters per second, the liquid velocity in the downcomer is between 2.0 and 2.5 meters per second, the liquid velocity in the lower section of the riser is between 0.3 and 0.6 meters per second and the liquid velocity in the upper section of the riser is between 2.0 and 2.5 meters per second.

4. A method according to claim 1, wherein the area of the gas disengagement section is greater than the cross-sectional area of the downcomer.

* * * * *